US00PP32725P2

(12) United States Plant Patent

Llosá Llácer et al.

(10) Patent No.: US PP32,725 P2
(45) Date of Patent: Jan. 5, 2021

(54) *CANNABIS* PLANT NAMED 'PAN2020'

(50) Latin Name: ***Cannabis sativa* (L.)**
Varietal Denomination: PAN2020

(71) Applicant: BIOMAX SEEDS S.L., Valencia (ES)

(72) Inventors: Ernesto Rafael Llosá Llácer, Valencia (ES); Salvador Soler Aleixandre, Valencia (ES)

(73) Assignee: BIOMAX SEEDS S.L., Valencia (ES)

( * ) Notice: Subject to any disclaimer, the term of this patent is extended or adjusted under 35 U.S.C. 154(b) by 0 days.

(21) Appl. No.: 16/602,514

(22) Filed: Oct. 22, 2019

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ... A01H 5/02; A01H 5/12; A01H 5/00; A01H 6/28; A61K 36/185
See application file for complete search history.

(56) References Cited

U.S. PATENT DOCUMENTS

| | | | |
|---|---|---|---|
| 9,370,164 | B2 | 6/2016 | Lewis et al. |
| PP27,475 | P2 | 12/2016 | Kubby et al. |
| PP30,434 | P3 | 4/2019 | Alfred et al. |
| PP30,639 | P2 | 7/2019 | Stanley et al. |
| PP30,668 | P3 | 7/2019 | Holmes et al. |
| 2014/0259228 | A1 | 9/2014 | Cohen et al. |
| 2017/0172040 | P1 | 6/2017 | Carter et al. |
| 2018/0295804 | A1 | 10/2018 | Muck et al. |
| 2019/0000029 | A1 | 1/2019 | Leo et al. |
| 2019/0090404 | P1 | 3/2019 | Cohen et al. |
| 2019/0183003 | P1 | 6/2019 | Lewis et al. |
| 2019/0183004 | P1 | 6/2019 | Lewis et al. |
| 2019/0183005 | P1 | 6/2019 | Lewis et al. |
| 2019/0183006 | P1 | 6/2019 | Lewis et al. |
| 2019/0183007 | P1 | 6/2019 | Lewis et al. |
| 2019/0183008 | P1 | 6/2019 | Lewis et al. |
| 2019/0183009 | P1 | 6/2019 | Lewis et al. |
| 2019/0183010 | P1 | 6/2019 | Lewis et al. |
| 2019/0230882 | A1 | 8/2019 | Fletcher et al. |
| 2019/0254213 | P1 | 8/2019 | Lewis et al. |

FOREIGN PATENT DOCUMENTS

WO 2019113497 A1 6/2019

OTHER PUBLICATIONS

Buddha Seeds First THC-free strain with high CBG, 2019, retrieved on Apr. 15, 2020, retrieved from the Internet at http://www.buddhagenetics.com/thc-free-high-cbg-strains/, 3 pp. (Year: 2019).*
Trademarkv Electronic Search System (TESS) retrieved on Apr. 16, 2020, retrieved from the Internet at http://tmsearch.uspto.gov/bin/showfield?f=doc&state=4810:tkdlll.2.4, 2 pp. (Year: 2020).*
Trademark Manual of Examining Procedure (Oct. 2018) retrieved at https://tmep.uspto.gov/RDMS/TMEP/current#/current/TMEP-1200d1e2820.html, 2 pp. (Year: 2018).*
Upov International Union for the Protection of New Varieties of Plants Explanatory Notes on Variety Denominations Under the Upov Convention 2015, retrieved from the Internet at https://www.upov.int/edocs/infdocs/en/upov_inf_12.pdf, pp. 1, 3-8. (Year: 2015).*
G. Fournier, "Identification of a New Chemotype in *Cannabis sativa*: Cannabigerol—Dominant Plants, Biogenetic and Agronomic Prospects", Nov. 6, 1986, 277-280, Planta Medica 1987.
Salvador Soler, "Use of Embryos Extracted from Individual *Cannabis sativa* Seeds for Genetic Studies and Forensic Applications", journal, Mar. 2016, 494-500, Journal of Forensic Sciences, vol. 61, No. 2.
Salvador Soler, "Genetic Structure of *Cannabis sativa* var. indica Cultivars Based on Genomic SSR (gSSR) Markers: Implications for Breeding and Germplasm Management", journal, 2017, 171-178, Industrial Crops and Products, ScienceDirect.
E.P.M. De Meijar, "The Inheritance of Chemical Phenotype in *Cannabis sativa* L. (II): Cannabigerol Predominant Plants" 2005, 189-198, Euphytica (2005), Springer.

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of *Cannabis sativa* (L.), named 'PAN2020' is characterized by its unique cannabinoid profile, specifically with respect to its high cannabigerol (CBG) content and lack of tetrahydrocannabinol (THC) and cannabidiol (CBD). The new variety resulted from the cross breeding of two *Cannabis sativa* (L.) clones performed by the inventor and has been asexually reproduced to ensure the resulting clones exhibit the same features and properties as the parent.

8 Drawing Sheets

*CANNABIS* PLANT NAMED 'PAN2020'

Latin name of genus and species: *Cannabis sativa* (L.).
Variety denomination: PAN2020.

BACKGROUND

*Cannabis* has many medical and therapeutic uses. For example, *Cannabis* has successfully been used to help relieve nausea and vomiting in patients undergoing chemotherapy treatment. *Cannabis* also has efficacy as an antiemetic as compared to other currently available pharmaceutical products.

*Cannabis sativa* (L.) contains several chemical compounds that are part of the cannabinoid family. Namely, the following five compounds can be found in *Cannabis sativa* (L.): cannabidiol (CBD), cannabichromene, cannabigerol (CBG), Δ-9-tetrahydrocannabinol (THC), and cannabinol. Cannabinoids from *C. sativa* (L.) are known for their antibacterial potential as well as other useful properties. CBG is of particular interest as an extract of *Cannabis sativa* (L.). However, all currently known species of *Cannabis* plant contain 1.9% or less CBG by weight.

CBG is the non-acidic form of cannabigerolic acid, the parent molecule from which other cannabinoids are synthesized. CBG has the following chemical formula:

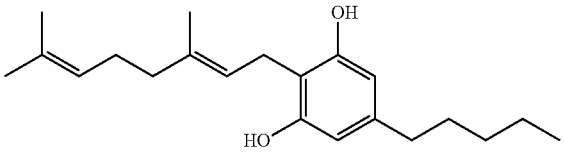

(Chemical Formula of CBG ($C_{21}H_{32}O_2$)

SUMMARY

Variety PAN2020 was developed in Valencia, Spain. This new variety was developed under the project "Obtención de variedades de cáñamo (*Cannabis sativa* var. *sativa*) con elevado contenido en fitocannabinoides de interes terapéutico".

Briefly, a screening was performed to evaluate somaclonal variation ability of a collection of *Cannabis sativa*. An individual plant was selected by its high load capacity for callus induction and plant regeneration from leaves and cotyledons segments. An unusual cannabinoid profile (cannabigerol as predominant cannabinoid without the presence of tetrahydrocannabinol) was identified in one of the regenerated somaclones. In order to increase cannabigerol accumulation, the somaclone was crossed with a resinous individual and the resulting F2 progeny was evaluated. The individual plant with the greatest cannabinoid accumulation was then selected.

BRIEF DESCRIPTION OF THE DRAWINGS

The accompanying photographs illustrate features of the new 'PAN2020' variety. Additionally, experimental data obtained from extracts of the new varietal illustrate unique features of the plant, specifically its cannabinoid profile.

Colors in the photographs may differ slightly from the color values cited in the botanical description.

DETAILED BOTANICAL DESCRIPTION

Following is a detailed description of the botanical and analytical chemical characteristics of the new variety. The information for this botanical description was either collected or verified during the growing seasons of 2018-2019 in the growing areas of Valencia, Spain.

It should be noted that botanical characteristics, and to a lesser degree the analytical characteristics, are somewhat dependent on cultural practices and climatic conditions and can vary with location or year.

Figure 15:
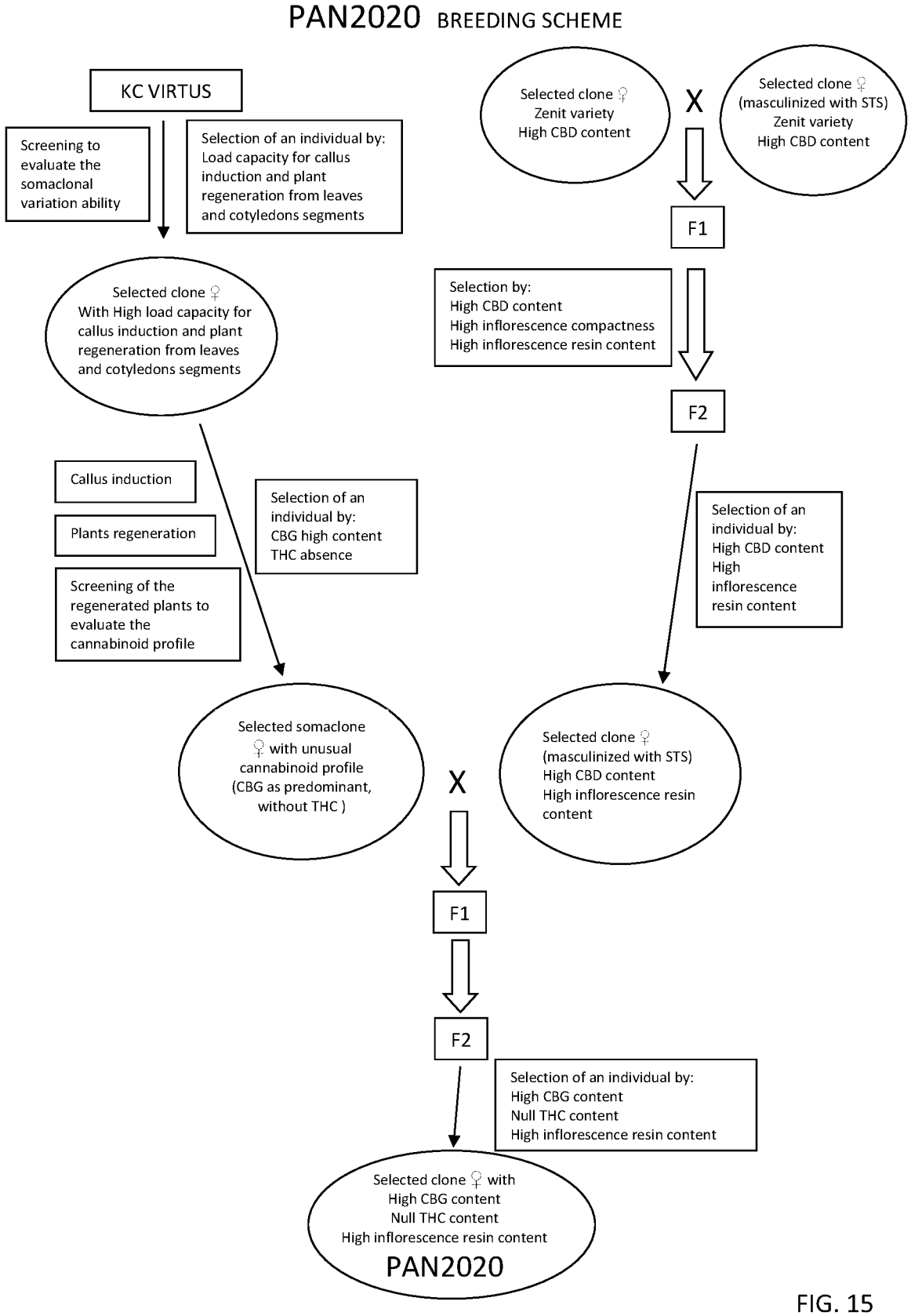
FIG. 15 shows the breeding scheme of the new variety.

Parentage: The new variety is the result of multiple generational crosses originally using 'KC VIRTUS' (not patented) and 'ZENIT' (not patented). To develop the new PAN2020 variety, a screening was first performed to evaluate somaclonal variation ability in 'KC VIRTUS'. An individual plant from the 'KC VIRTUS' somaclonal variation screen was selected by its high load capacity for callus induction and plant regeneration from leaves and cotyledons segments. This individual plant underwent callus induction and plant regeneration and then cannabinoid profile screening was conducted on the regenerated plants. An unusual cannabinoid profile (cannabigerol (CBG) as predominant cannabinoid without the presence of tetrahydrocannabinol (THC)) was identified in one of the regenerated somaclones. This selected regenerated somaclone was then crossed with a masculinized female plant selected from an F2 cross from 'ZENIT' x 'ZENIT'. The resulting F1 progeny were crossed to create an F2 progeny and individual plants within that F2 progeny were evaluated. The individual plant with the greatest cannabinoid accumulation and the desired cannabinoid profile was then selected as the new variety. FIG. 15 outlines the detailed breeding scheme.

Locality where grown and observed: Variety PAN2020 was developed in Valencia, Spain.

Plant characteristics:

*Species.*—*Cannabis sativa* (L.).

*Plant life forms.*—Annual, herbaceous, dioecious flowering shrub, with prolific lateral branching.

*Plant growth habitat.*—An upright, tap-rooted annual plant, forming fibrous roots when asexually propagated.

*Plant origin.*—Cross of two proprietary clones.

*Plant propagation*.—Asexually propagated by vegetative cuttings and cloning.
*Propagation ease*.—Easy.
*Time to initiate roots*.—10 days at 25° C. and 18 hours of light per day.
*Height*.—0.9-2.0 m.
*Width*.—0.6-1.4 m.
*Plant vigor*.—Medium.
*Time to harvest*.—12 weeks.
*Resistance to pests or diseases*.—Not tested.
*Genetic modification*.—No.

Leaf characteristics:
*Leaf arrangement*.—Alternate.
*Leaf shape*.—Palmately compound (digitate).
*Leaf structure*.—Linear-lanceolate leaflets with glandular hairs.
*Leaf margins*.—Serrated.
*Leaf hairs*.—Present, sessile glandular trichomes.
*Leaf length with petiole at maturity*.—18-23 cm.
*Petiole length at maturity*.—4-9 cm.
*Petiole color*.—Pantone No. 7492 U.
*Petiole anthocyanin intensity*.—Weak.
*Petiole trichome type*.—Non-glandular, cystolithic and non-cystolithic.
*Stipule length at maturity*.—4 mm.
*Stipule shape*.—Acuminate.
*Stipule color*.—Pantone No. 583 U.
*Number of leaflets*.—3 to 5.
*Middle largest (longest) leaflet length*.—11-15 cm.
*Middle largest (longest) leaflet width*.—2-2.6 cm.
*Middle largest (longest) leaflet length/width ratio*.—15:2.6.
*Number of teeth of middle leaflet (average)*.—25.
*Leaf color (upper side)*.—Pantone No. 377 U.
*Leaf color (lower side)*.—Pantone No. 383 U.
*Leaf glossiness*.—Light.
*Vein/midrib shape*.—A central vein in each leaflet; oblique veins from the central vein to the tips of each serration of the margin.
*Vein/midrib color*.—Pantone No. 7492 U.
*Aroma*.—Low, spicy and woody; the major terpene is beta-Caryophyllene.

Stem characteristics:
*Stem shape*.—Round.
*Stem diameter at base*.—1.5-3.0 cm.
*Stem color*.—Pantone No. 583U.
*Branch strength*.—Medium to weak, flexible.
*Stem's internode length*.—Medium.
*Stem's depth of grooves*.—Shallow.
*Stem's trichome type*.—Non-glandular, cystolithic and non-cystolithic.
*Stem's amount of pitch in cross-section*.—Thick.

Inflorescence characteristics:
*Flowering (blooming) habit*.—Elliptical shaped racemose inflorescence, made up of a cluster of false spikes with single flowers.
*Proportion of female plants*.—100%.
*Inflorescence position*.—Axillary and terminal.
*Flower arrangement*.—Overlapping, touching, congested.
*Number of flowers per plant*.—Thousands.
*Number of flowers per inflorescence*.—Approximately 1000.
*Flower shape*.—A small green bract enclosing the ovary, with two slender stigmas sticking out of the bract, without petals or sepals.
*Flower (individual pistilate) length*.—6 mm.
*Flower (compound cyme) diameter*.—60 mm.
*Flower fragrance*.—Not very strong, floral, spicy, and woody; the major terpene is beta-Caryophyllene.
*Corolla*.—Absent.
*Bract shape*.—Urceolate.
*Bract color*.—Pantone No. 7496U.
*Bract size*.—9 mm on average.
*Bract trichome type*.—Glandular capitate-sessile and capitate-stalked, non-glandular cystolithic.
*Bracteole average size*.—6 mm on average.
*Bracteole shape*.—Beaked, urceolate.
*Bracteole trichome type*.—Glandular capitate-sessile and capitate-stalked, non-glandular cystolithic.
*Bracteole color*.—Pantone No. 584 U.
*Calyx*.—No defined calyx.
*Stigma shape*.—Slender, acuminate.
*Stigma length*.—8 mm.
*Stigma color*.—Pantone No. 5865 U.
*Trichome mature color*.—Pantone No. Cool grey 1 U.
*Trichome immature color*.—Cristal transparent.
*Terminal bud shape*.—Elliptical.
*Terminal bud color*.—Pantone No. 7496 U.
*Pedicel*.—Absent.
*Staminate shape*.—N/A.
*Pollen*.—Absent.
*Seed*.—4 mm; marbled achene, Pantone No. 469 U in color.
*Petals*.—Apetalus.
*Max thc content*.—Not detected.
*Max cbd content*.—Not detected.
*Max cbg content*.—14-17%.

Other characteristics:
*Time period offlowering/blooming*.—7-9 weeks.
*Hardiness of plant*.—Not tested.
*Breaking action*.—Flexible, elastic.
*Rooting rate after cutting/cloning*.—99.
*Flower shipping quality*.—High.
*Flower storage life*.—Long.
*Flower market use*.—Extracts, concentrates, tinctures, oils, topicals.
*Productivity of the flower (weight/plant)*.—250 g/plant.

Analytical Data

Extracts from the presently disclosed 'PAN2020' variety were obtained and analyzed using gas chromatography techniques. The samples were tested using an Agilent 7820 gas chromatograph with a flame ionization detector (FID). The samples were each prepared using Prazepam as an internal standard.

Figure 1:
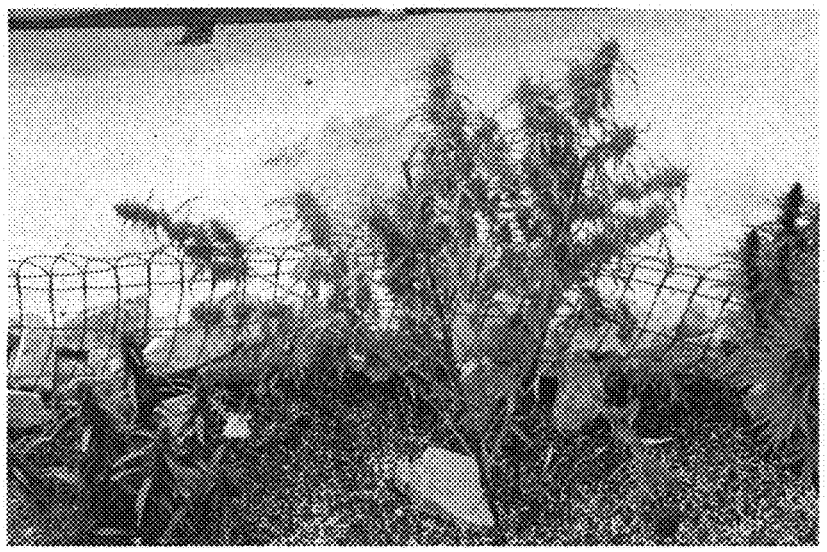
FIGS. 1 and 2 depict the appearance of the whole plant during growth.
Figure 2:
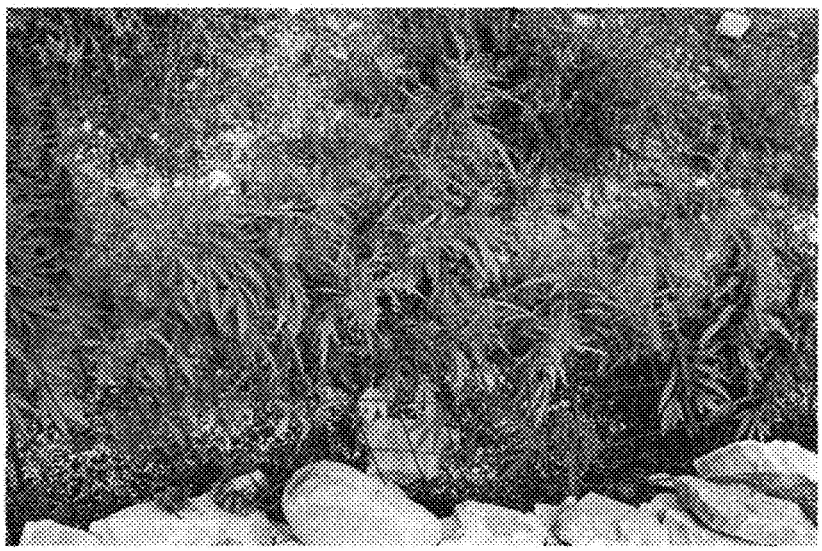
Figure 3:
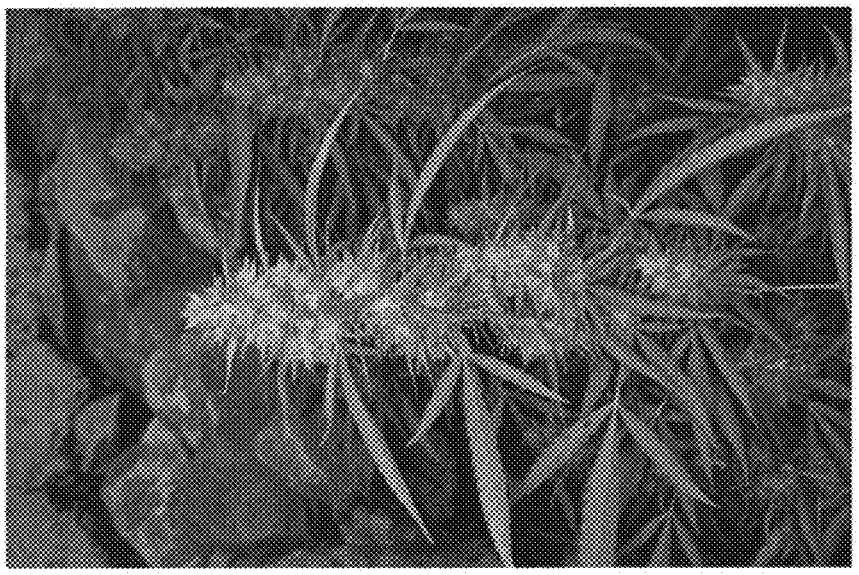
FIG. 3 depicts a top view of a lateral branch.
Figure 4:
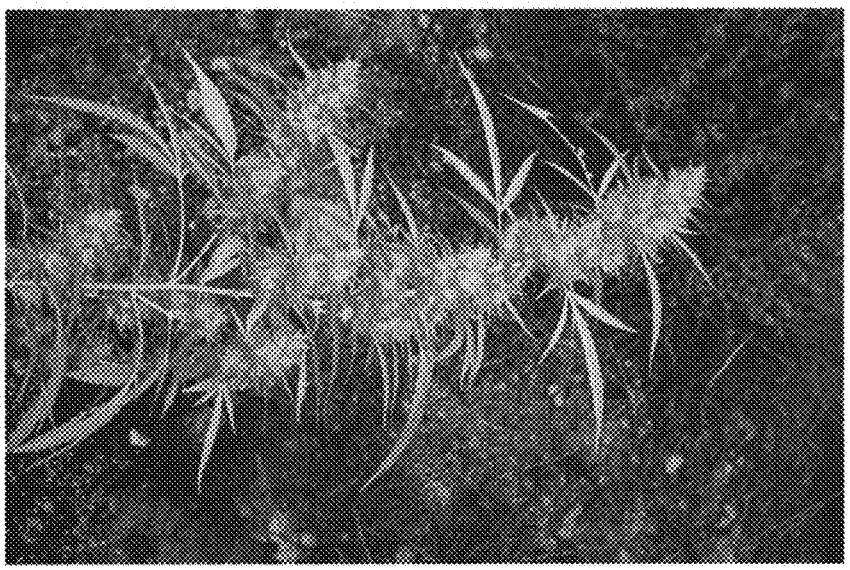
FIG. 4 depicts a bottom view of a lateral branch.
Figure 5:
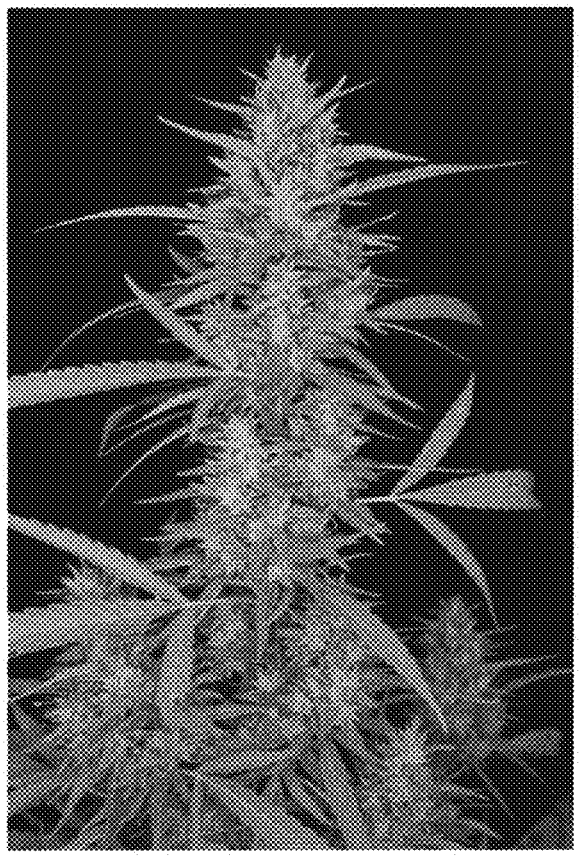
FIG. 5 depicts flowers of the plant.
Figure 6:
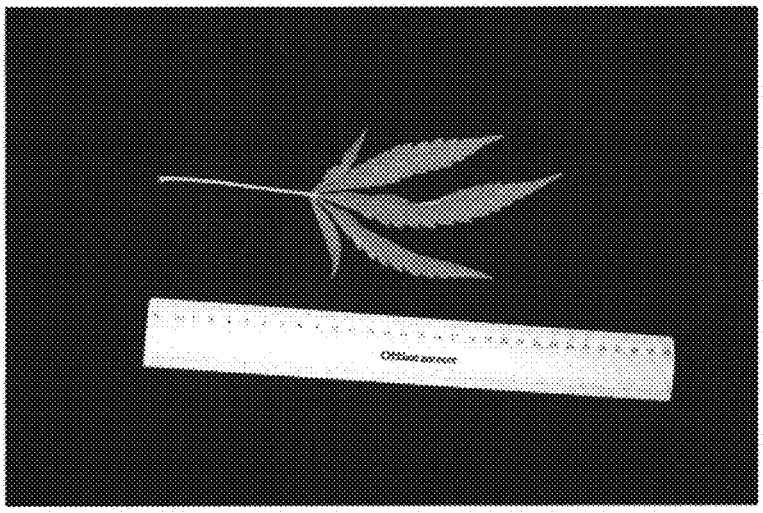
FIGS. 6 and 7 depict distinct fan-shaped leaves, shown with a ruler to indicate scale.
Figure 7:
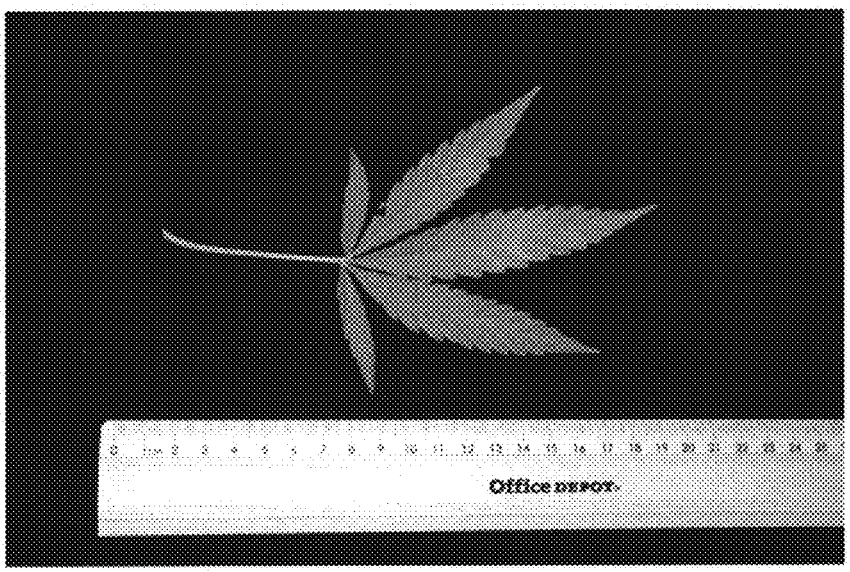
Figure 8:
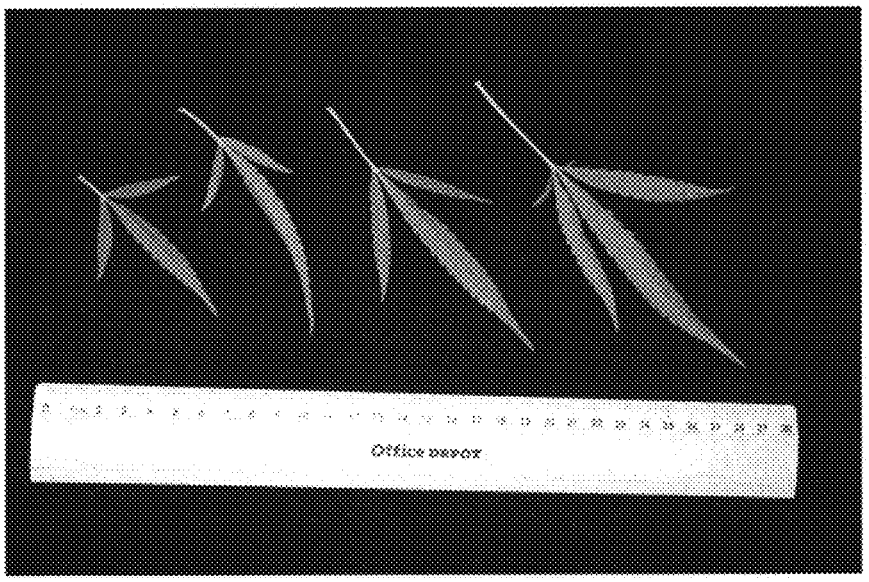
FIG. 8 depicts small leaves of the plant, shown with a ruler to indicate scale.
Figure 9:
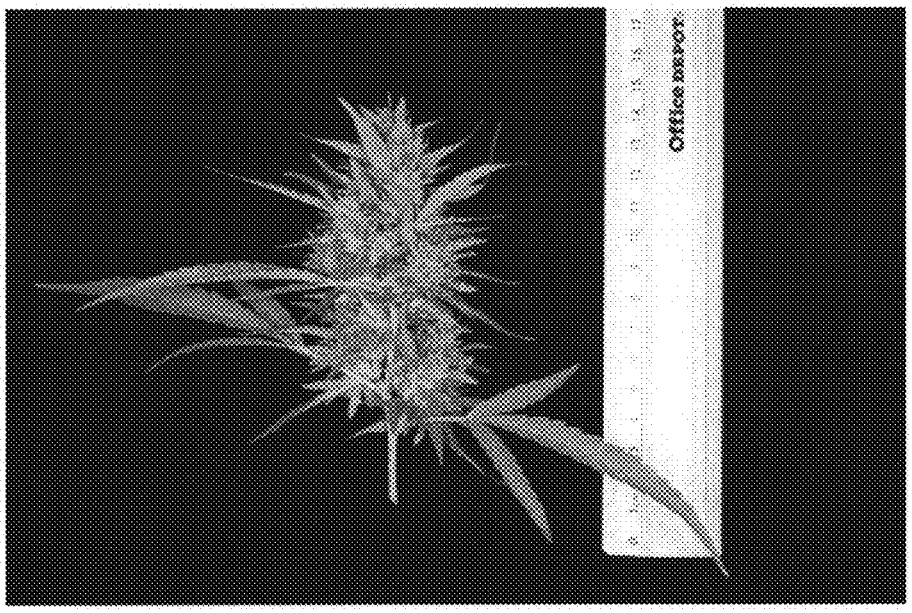
FIG. 9 depicts a close-up detail of a flower, shown with a ruler to indicate scale.
Figure 10:
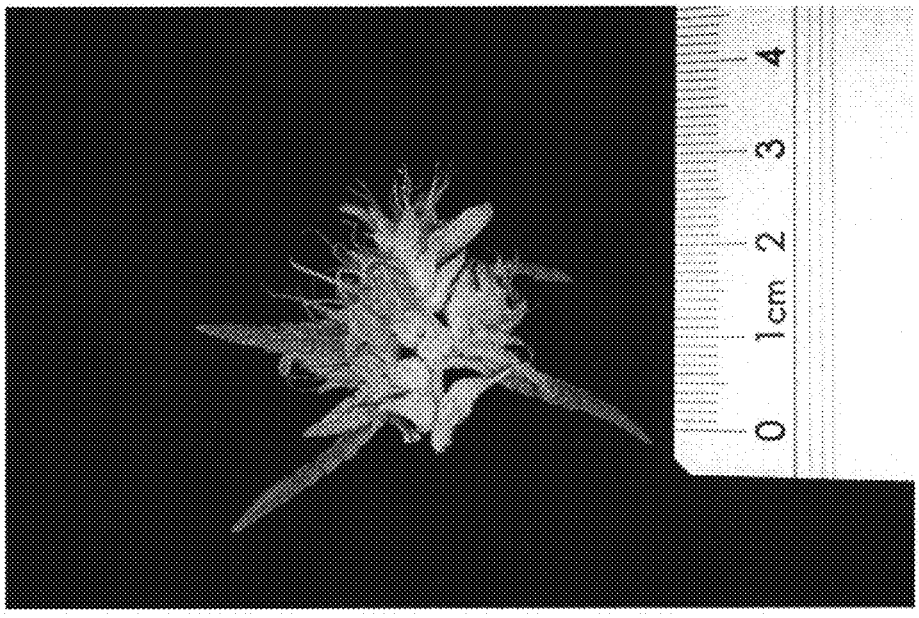
FIG. 10 depicts a close-up detail of a flower, shown with a ruler to indicate scale.
Figure 11:
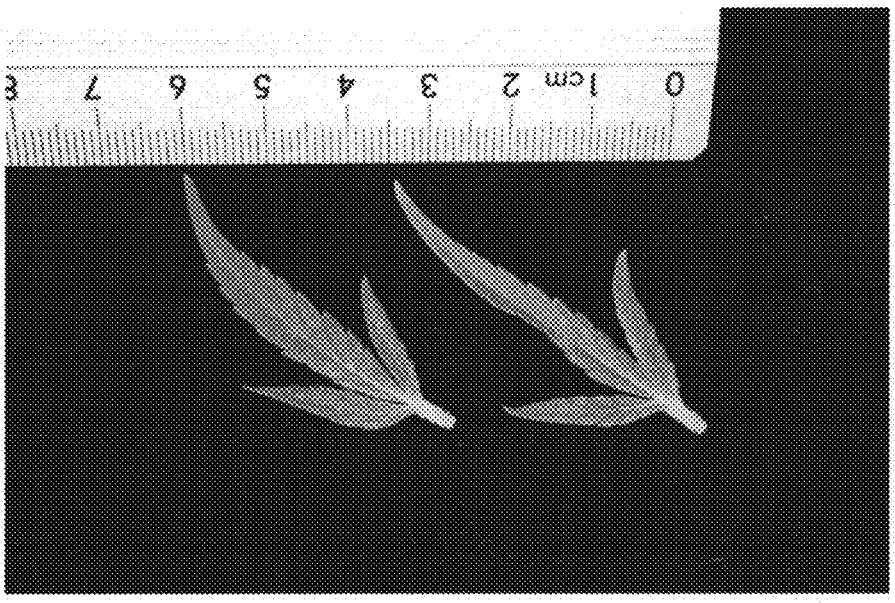
FIG. 11 depicts two flower leaves, shown with a ruler to indicate scale.
Figure 12:
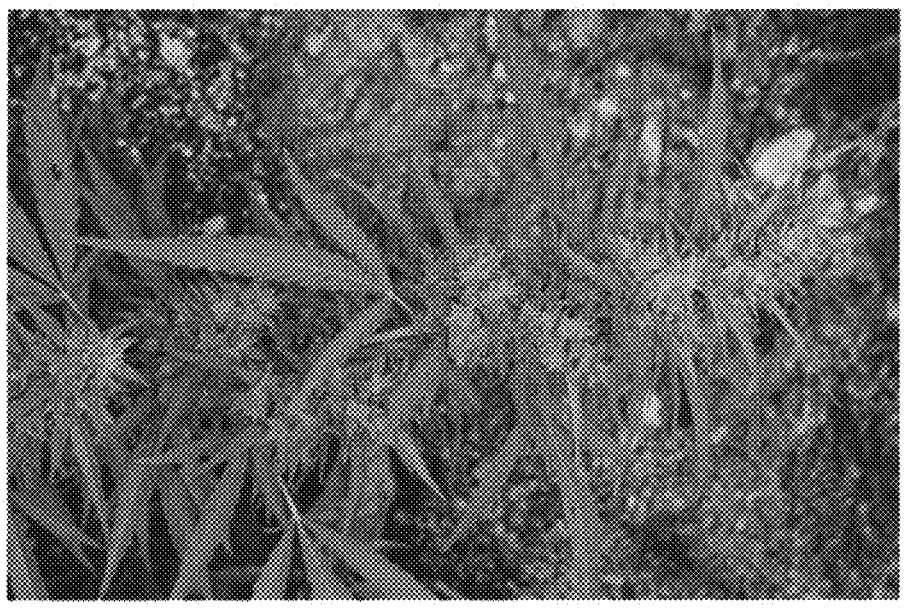
FIG. 12 depicts a lateral branch of the plant.
Figure 13:
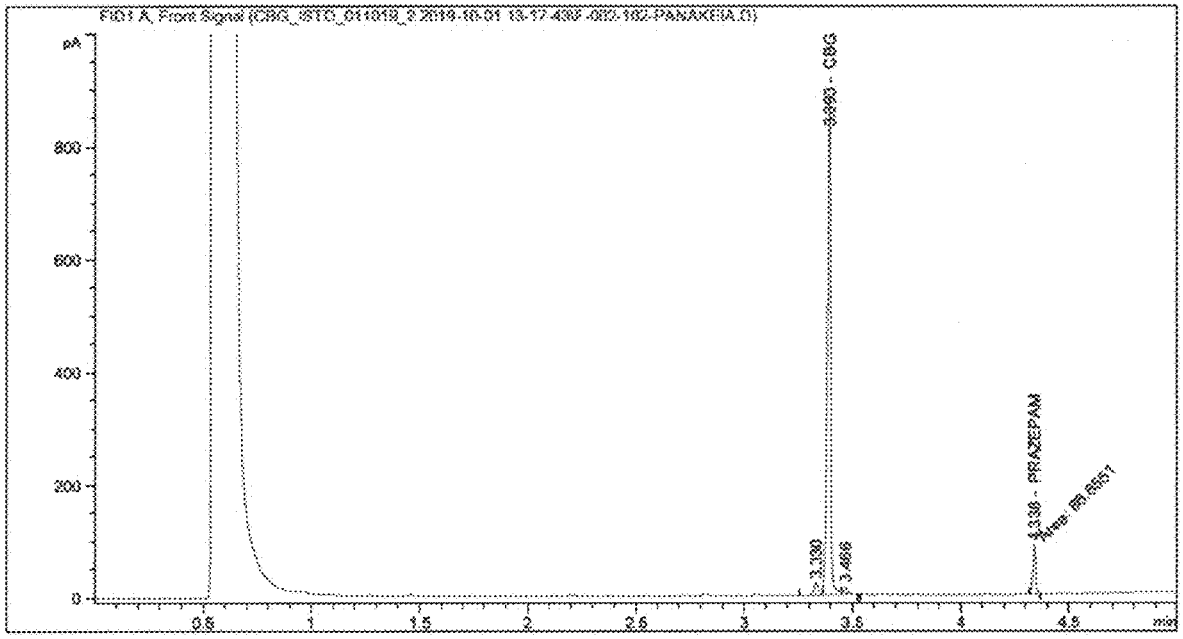
FIG. 13 shows a chromatogram of a first sample extracted from the plant.
Figure 14:
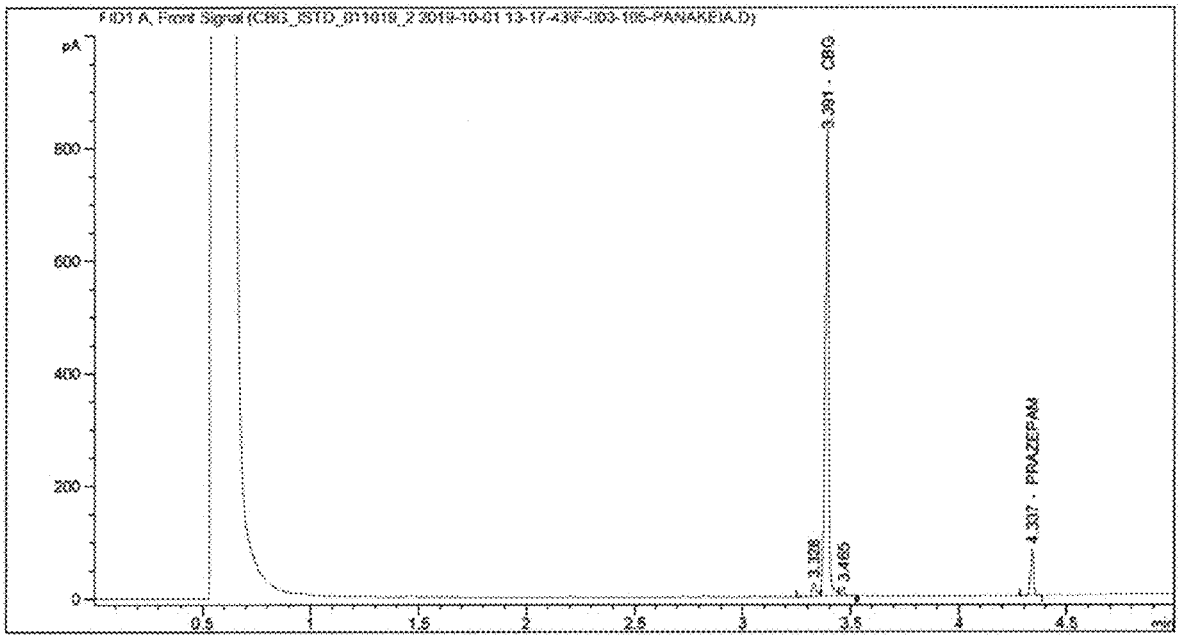
FIG. 14 shows a chromatogram of a second sample extracted from the plant.

FIG. 13 shows a chromatogram of the data obtained from a first extract of the varietal and FIG. 14 shows of chromatogram of the data obtained from a second extract of the varietal. Table 1, shown below, illustrates the calculated area under the peaks shown in the chromatogram of FIG. 13 and Table 2 illustrates the calculated area under the peaks shown in FIG. 14.

TABLE 1

Area under the Peaks of Sample Chromatogram Shown in FIG. 13

| RetTime [min] | Type | ISTD used | Area [pA * s] | Amt/ Area ratio | Amount % | Grp | Name |
|---|---|---|---|---|---|---|---|
| 2.896 | | 1 | — | — | — | | CBD |
| 3.304 | | 1 | — | — | — | | THC |
| 3.393 | VV R+ | 1 | 1059.28174 | 1.00250 | 17.911460 | | CBG |
| 3.571 | | 1 | — | — | — | | CBN |

TABLE 1-continued

Area under the Peaks of Sample Chromatogram Shown in FIG. 13

| RetTime [min] | Type | ISTD used | Area [pA * s] | Amt/ Area ratio | Amount % | Grp | Name |
|---|---|---|---|---|---|---|---|
| 4.338 | MF I | 1 | 88.85506 | 1.00000 | 0.014987 | | PRAZE-PAM |
| Totals without ISTD(s): | | | | | 17.911460 | | |

As shown in FIG. 13 and Table 1, the first sample tested contained approximately 17.91% CBG.

TABLE 2

Area under the Peaks of Sample Chromatogram Shown in FIG. 14

| RetTime [min] | Type | ISTD used | Area [pA * s] | Amt/ Area ratio | Amount % | Grp | Name |
|---|---|---|---|---|---|---|---|
| 2.896 | | 1 | — | — | — | | CBD |
| 3.304 | | 1 | — | — | — | | THC |
| 3.391 | VV R+ | 1 | 973.45337 | 1.00305 | 17.054502 | | CBG |
| 3.571 | | 1 | — | — | — | | CBN |
| 4.337 | BB I | 1 | 86.11620 | 1.00000 | 0.015041 | | PRAZE-PAM |
| Totals without ISTD(s): | | | | | 17.054502 | | |

As shown in FIG. 14 and Table 2, the second sample tested contained approximately 17.05% CBG.

The presently disclosed variety thus has a much higher CBG content than previously known varieties of *Cannabis sativa* (L.), making it a promising candidate as a new source of CBG. Additionally, the unique cannabinoid profile of this variety could prove useful in medical applications as well as for other possible applications.

Propagation Status

Asexual plant propagation has been demonstrated for the disclosed varietal at Valencia, Spain. Specifically, from a selected individual plant, stem portions were cut with at least two knots with axillary shoots. The bark of the lower portion was slightly scraped to expose the cambium. The lower portion of the cuttings was introduced into a solution containing the auxins NAA and IBA (naphthaleacetic acid and indolbutyric acid). The cuttings were introduced into a rooting substrate (peat) previously moistened with water of low electrical conductivity (<0.1 mS/cm) to field capacity, leaving buried at least one of the nodes. The cuttings were placed under conditions of low illuminance (500 lux) and high relative humidity (>90%) with a photoperiod of 18/6 hours (i.e., 18 hours of light followed by six hours of darkness). To promote the emission of roots, a background heat source was placed so that the buried part of the cuttings was kept at a temperature 3 degrees higher than that of the aerial part. The material was sprayed regularly with water of low electrical conductivity (<0.1 mS/cm) and in 10 days at 25° C., the first roots were seen.

An assay growing 20 clones of the new variety was performed in indoor conditions (18 hours light/6 hour dark, at 60% relative humidity and 25° C.). Two months after, the photoperiod was changed to 12 hours light followed by 12 hours dark to induce plants flowering. All plants needed 60 days to finish the flowering stage. Analysis of cannabinoid content indicated that all plants accumulated cannabigerol (CBG) as the predominant cannabinoid without the presence of tetrahydrocannabinol (THC). Thus, the clones had the same properties as the parent.

Genetic stability of clones was analysed using 13 genomic Single Sequence Repeats (gSSR) markers (CSG01, CSG03, CSG05, CSG10, CSG12, CSG13, CSG14, CSG15, CSG18, CSG20, CSG22, CSG24 and CSG25) and the methodology described in Soler, S. et al., Use of embryos extracted from individual *Cannabis sativa* seeds for genetic studies and forensic applications. *J. Forensic Sci.* 61, 494-500 (2016) and Soler, S. et al., Genetic structure of *Cannabis sativa* var. *indica* cultivars based on genomic SSR (gSSR) markers: Implications for breeding and germplasm management, *Industrial Crops & Products,* 104, 171-178 (2017). The experimental results indicated a total genetic stability in all clones tested.

DISTINGUISHING CHARACTERISTICS

The new variety of the present invention can readily be distinguished from its ancestors. More specifically, 'KC VIRTUS' (i.e., the seed grandparent), 'ZENIT' (i.e., the pollen grandparent), the male parent (i.e., resinous individual), and the female parent (i.e., selected regenerated somaclone) provide a different chemotype and cannabinoid content compared to the new variety, as shown in the Table 3, below.

TABLE 3

| Variety | CBG Content | THC Content | CBD Content |
|---|---|---|---|
| 'KC VIRTUS' | LOW | LOW | LOW |
| 'ZENIT' | | | HIGH |
| Male Parent (resinous individual) | LOW | LOW | HIGH |
| Female Parent (selected regenerated somaclone) | MEDIUM | NULL | LOW |
| 'PAN2020' | HIGH | NULL | NULL |

Moreover, the new variety can readily be distinguished from related similar non-parental/grandparental varieties due to its high CBG content and total absence of THC. This new *Cannabis sativa* variety 'PAN2020' can be distinguished from all other known *Cannabis* varieties known to the Inventor by its unusual cannabinoid profile. Specifically, PAN2020 contains cannabigerol (CBG) as the predominant cannabinoid without the presence of tetrahydrocannabinol (THC) and without the presence of cannabidiol (CBD). For example, 'HOLY CRUNCH' (U.S. Pat. No. 31,874) has 6.6-16.7% THC, 6.5-15.3% CBD, and 0.25-1.9% CBG.

What is claimed is:

1. A new and distinct *Cannabis* plant of the species *Cannabis sativa* (L.), named 'PAN2020', as herein described and illustrated.

* * * * *